(12) United States Patent
Dominguez-Manzanares

(10) Patent No.: US 7,652,064 B2
(45) Date of Patent: *Jan. 26, 2010

(54) AMPA RECEPTOR POTENTIATORS

(75) Inventor: Esteban Dominguez-Manzanares, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 346 days.

This patent is subject to a terminal disclaimer.

(21) Appl. No.: 11/422,473

(22) Filed: Jun. 6, 2006

(65) Prior Publication Data

US 2006/0276532 A1   Dec. 7, 2006

Related U.S. Application Data

(60) Provisional application No. 60/724,206, filed on Oct. 6, 2005.

(30) Foreign Application Priority Data

Jun. 6, 2005   (EP) .................................. 05380117
Aug. 18, 2005   (EP) .................................. 05380187

(51) Int. Cl.
*A61K 31/381*   (2006.01)
*C07D 333/10*   (2006.01)

(52) U.S. Cl. ........................... 514/447; 549/29; 549/68; 514/430; 514/438

(58) Field of Classification Search ................ 514/438, 514/447; 549/29, 68
See application file for complete search history.

(56) References Cited

U.S. PATENT DOCUMENTS 7,393,868 B2 *   7/2008   Castano Mansanet et al. .... 514/352

FOREIGN PATENT DOCUMENTS

| WO | WO 98/33496 | 8/1998 |
|---|---|---|
| WO | WO 01/42203 A1 | 6/2001 |
| WO | WO 02/32858 A1 | 4/2002 |
| WO | WO 02/098847 A1 | 12/2002 |
| WO | WO 02/100851 A2 | 12/2002 |
| WO | WO 03/010158 A1 | 2/2003 |
| WO | WO 2005/070916 A1 | 8/2005 |

OTHER PUBLICATIONS

Ornstein et al., "Biarylproplsulfonamides as Novel, Potent Potentiators of 2-Amino-3-(5-methyl-3-hydroxyisoxazol-4-yl)-propanoic Acid (AMPA) Receptors," *J. Med. Chem.*, vol. 43, pp. 4354-4358 (2000).

* cited by examiner

*Primary Examiner*—Golam M Shameem
(74) *Attorney, Agent, or Firm*—Tonya L. Combs

(57) ABSTRACT

The present invention relates to AMPA receptor potentiators of Formula I:

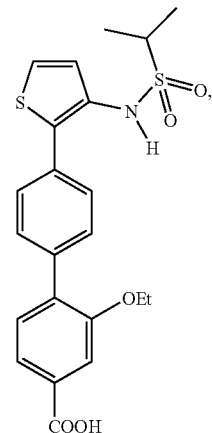

formulations comprising them, methods for their use, and intermediates useful for their preparation.

2 Claims, No Drawings

AMPA RECEPTOR POTENTIATORS

CROSS REFERENCE TO RELATED APPLICATIONS

This patent applicaton claims the benefit of priority under Title 35 United States Code, section 119(e), of EP Provisional Patent Application Number 05380117.1, Filed Jun. 6, 2005, EP Provisional Patent Application Number 05380187.4, filed Aug. 18, 2005 and U.S. Provisional Patent Application No. 60/724,206 filed Oct. 6, 2005.

BACKGROUND OF THE INVENTION

Glutamate is the major excitatory neurotransmitter in the central nervous system. Three glutamate receptor ion channel subtypes have been identified based on their sensitivity to the selective activators (agonists) N-methyl-D-aspartate (NMDA), α-amino -3-hydroxy-5-methyl-4-isoxazole propionic acid (AMPA), and kainate.

AMPA receptors mediate cellular responses to glutamate by direct and indirect mechanisms. When activated by glutamate or AMPA, AMPA receptor ion channels allow sodium ions ($Na^+$) and calcium ions ($Ca^{2+}$) to pass directly through the channel pore. In addition, AMPA receptor ion channels can facilitate the activation of NMDA receptors by initiating cellular depolarization that relieves magnesium ion ($Mg^{2+}$)-dependent block of NMDA receptors.

Multiple AMPA receptor subtypes have been identified and cloned: GluR1, GluR2, GluR3, and GluR4 as disclosed by Hollmann and Heinemann, *Ann. Rev. Neurosci.*, 17, 31-108 (1994). Each subunit consists of a sequence of approximately 900 amino acids. Four subunits are thought to assemble to form a tetrameric ion channel complex with the functional properties of this ion channel most likely being determined by its subunit composition.

Ion channel currents activated by glutamate via AMPA receptors are transient. The time course of currents is modified by refractory states caused during glutamate binding which is referred to as desensitization and by the rate of glutamate removal from the ion channel binding site which results in deactivation. Ion influx through AMPA receptors may be enhanced by compounds that either prevent desensitization or by compounds that slow deactivation rates. Compounds that enhance glutamate-stimulated ion influx at AMPA receptors are known as positive AMPA receptor allosteric modulators or AMPA receptor potentiators. One such compound, which selectively potentiates AMPA receptor function, is cyclothiazide. Since AMPA receptors play a pivotal role in mediating fast excitatory transmission in the central nervous system, molecules that enhance AMPA receptor function have multiple therapeutic targets.

Compounds that allosterically potentiate AMPA receptors have been shown to enhance synaptic activity in vitro and in vivo as disclosed, for example, by I. Ito, et al., *J. Physiol.*, 424, 533-543 (1990) and A. Copani, et al., *Journal of Neurochemistry*, 58, 1199-1204 (1992). Such compounds have also been shown to enhance learning and memory in rats, monkeys, and humans, and are reviewed by Gouliaev and Senning, *Brain Research Reviews*, 19, 180-222 (1994).

International Patent Application Publication WO 98/33496 published Aug. 6, 1998 discloses certain sulfonamide derivatives which are useful, for example, for treating psychiatric and neurological disorders, for example cognitive disorders, Alzheimer's disease, age-related dementias, age-induced memory impairment, tardive dyskinesia, Huntington's chorea, myoclonus, Parkinson's disease, reversal of drug-induced states (such as cocaine, amphetamines, alcohol-induced states), depression, attention deficit disorder, attention deficit hyperactivity disorder, psychosis, cognitive deficits associated with psychosis, and drug-induced psychosis. P. L. Ornstein, et al. *J. Med. Chem.*, 43, 4354 (2000) further disclose biarylpropylsulfonamides which are potent potentiators of AMPA receptors. In addition, X. Li, et al., *Neuropharmacology*, 40, 1028 (2001) disclose antidepressant-like actions of an AMPA receptor potentiators. D. D. Schoepp, et al. and Tizzano, et al., *Society for Neuroscience Abstracts*, 26(1-2), 528.19 and 528.20, 30th Annual Meeting, New Orleans, (Nov. 4-9, 2000) disclose an orally active AMPA receptor potentiator that enhances spatial learning and memory performance in rats, and reverses both pharmacologically and age-associated learning and memory deficit in rats.

New AMPA receptor potentiators are needed to treat these neurological disorders.

SUMMARY OF THE INVENTION

The present invention provides compounds of Formula I:

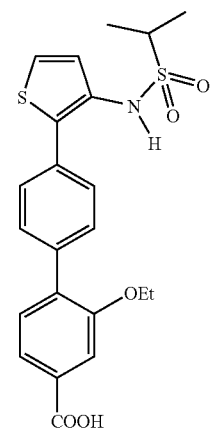

or a pharmaceutically acceptable salt thereof.

The present invention provides a compound of Formula I for use as a pharmaceutical. The present invention further provides a method of potentiating glutamate receptor function in a patient, which comprises administering to said patient in need of such treatment an effective amount of a compound of Formula I or a pharmaceutically acceptable salt thereof.

In addition, the present invention further provides a method of treating schizophrenia, cognitive deficits associated with schizophrenia, Alzheimer's disease, dementia of the Alzheimer's type, mild cognitive impairment, Parkinson's disease, or depression in a patient, which comprises administering to a patient in need of such treatment an effective amount of a compound of Formula I or a pharmaceutically acceptable salt thereof.

According to another aspect, the present invention provides the use of a compound of Formula I, or a pharmaceutically acceptable salt thereof, for the manufacture of a medicament for treating schizophrenia, cognitive deficits associated with schizophrenia, Alzheimer's disease, dementia of the Alzheimer's type, mild cognitive impairment, Parkinson's disease, or depression.

In addition, the present invention provides the use of a compound of Formula I, or a pharmaceutically acceptable salt thereof, for treating schizophrenia, cognitive deficits associated with schizophrenia, Alzheimer's disease, dementia of the Alzheimer's type, mild cognitive impairment, Parkinson's disease, or depression.

The invention further provides pharmaceutical compositions comprising, a compound of Formula I, or a pharmaceutically acceptable salt thereof, and a pharmaceutically acceptable carrier, diluent, or excipient.

Additionally, the use of a compound of Formula I in conjunction with antipsychotics, antidepressants, and drugs useful in treating cognitive disorder is contemplated within the scope of the present invention. WO 2005/040110 teaches the use of compounds that potentiate glutamate receptor function in conjunction with antipsychotics, antidepressants and drugs useful in treating cognitive disorder.

DETAILED DESCRIPTION OF THE INVENTION

As used herein the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by a compound of Formula I and a pharmaceutically acceptable salt thereof through their action as potentiators of glutamate receptor function. Such conditions include those associated with glutamate hypofunction, such as psychiatric and neurological disorders, for example cognitive disorders and neuro-degenerative disorders such as Alzheimer's disease; dementia of the Alzheimer's type, age-related dementias; age-induced memory impairment; cognitive deficits due to autism, Down's syndrome and other central nervous system disorders with childhood onset, cognitive deficits post electroconvulsive therapy, movement disorders such as tardive dyskinesia, Huntington's chorea, myoclonus, dystonia, spasticity, Parkinson's disease; reversal of drug-induced states (such as cocaine, amphetamines, alcohol-induced states); depression; attention deficit disorder; attention deficit hyperactivity disorder; psychosis such as schizophrenia; cognitive deficits associated with psychosis such as schizophrenia, drug-induced psychosis, stroke, and sexual dysfunction. Compounds of Formula I may also be useful for improving memory (both short term and long term) and learning ability. The present invention provides the use of a compound of Formula I for the treatment of each of these conditions.

It is understood by one of ordinary skill in the art that cognition includes various "domains." These domains include short-term memory, long term memory, working memory, executive function, and attention. As used herein the term "cognitive disorder" is meant to encompass any disorder characterized by a deficit in one or more of the cognitive domains, including but not limited to short term memory, long term memory, working memory, executive function, and attention. It is further understood that the term "cognitive disorder" includes, but is not limited to the following specific disorders: age-related cognitive decline, mild cognitive impairment, Alzheimer's disease, dementia, dementia of the Alzheimer's type, Parkinson's dementia, Lewy Body dementia, substance-induced persisting dementia, alcohol-induced persisting dementia, alcohol-induced cognitive impairment, AIDS-induced dementia, learning disorders, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, cognitive deficits associated with amylotrophic lateral sclerosis, and cognitive deficits associated with multiple sclerosis. Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)).

The fourth edition of the Diagnostic and Statistical Manual of Mental Disorders (DSM-IV) (1994, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the International Statistical Classification of Diseases and Related Health Problems, tenth revision (ICD-10) (1992, World Health Organization, Geneva) and that terminology and classification systems evolve with medical scientific progress.

The present invention includes the pharmaceutically acceptable salts of a compound defined by Formula I. A compound of this invention can possess a sufficiently acidic group, and accordingly react with any of a number of organic and inorganic bases to form a pharmaceutically acceptable salt. The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable organic or inorganic base. Such salts are known as base addition salts. Such salts include the pharmaceutically acceptable salts listed in *Journal of Pharmaceutical Science*, 66, 2-19 (1977), which are known to the skilled artisan. Magnesium, diethylamine, hemipiperazine, and tert-butylamine salts are preferred. The tert-butylamine salts are most preferred.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention. The specific stereoisomers and enantiomers of compounds of Formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Certain classes of compounds of Formula I are preferred AMPA potentiaters. The following paragraphs describe such preferred classes:

a) The compound of Formula I is a free acid;

b) The compound of Formula I is a salt;

c) The compound of Formula I is a hydrate;

d) The compound of Formula I is an anhydrate;

e) The compound of Formula I is the hemipiperazine salt;

f) The compound of Formula I is the diethylamine salt;

g) The compound of Formula I is the tert-butylamine salt.

A compound of Formula I as the free acid is especially preferred.

The compound of the present invention can be prepared by a variety of procedures, some of which are illustrated in the schemes and examples below.

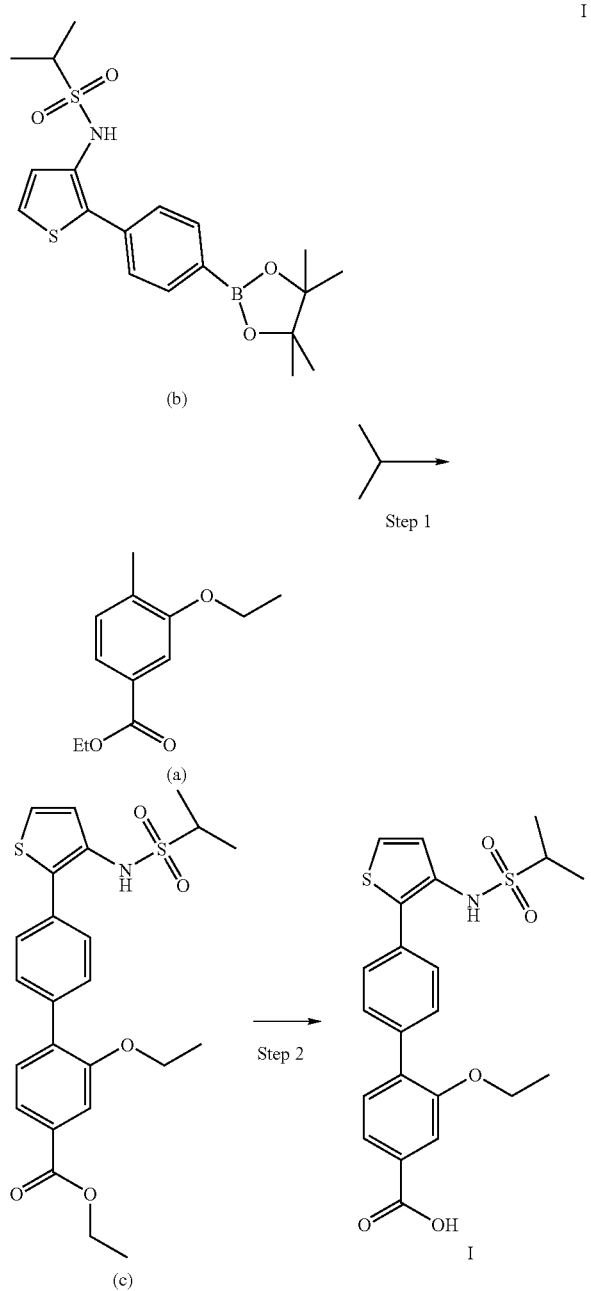

general cross-coupling techniques and for methods for preparing suitable starting materials and reagents.

More specifically, the compound of structure (a) is combined with about 1.0 to 1.5 equivalents of the suitable phenyl boronic acid or ester (b) in a suitable organic solvent or a suitable mixture of solvents. Examples of suitable organic solvents include 1,4-dioxane, dimethoxyethane (DME), DMF, benzene, toluene, acetone, ethanol (EtOH), heptane and the like. Examples of suitable solvent mixtures include DME/EtOH, THF/Water, Ethyl Acetate (AcOEt)/Water, Methanol (MeOH)/Water and the like. A suitable catalyst, such as tetrakis(triphenylphosphine)palladium, dichlorobis(triphenylphosphine)-palladium (II), $Pd(PCy_3)_2Cl_2$, or [1,1-bis(diphenylphospino)ferrocene]dichloro-palladium(II) or palladium black and a suitable base, for example sodium carbonate, or potassium acetate (AcOK), are added to the reaction mixture with stirring.

Step 2 of Scheme 1 demonstrates the hydrolysis of an ester of structure (e) to form a carboxylic acid of Formula I under conditions well known to the skilled artisan. For example, the compound of structure (e) is combined with an excess of lithium hydroxide or sodium hydroxide in a suitable solvent or solvent mixture, such as THF:water (2:1), THF:MeOH:Water (3:2:1), or water. To this mixture is added an excess of ($C_1$-$C_4$) alkanol, such as methanol, ethanol, propanol, or n-butanol, and the reaction is stirred at room temperature for about 1 to 24 hours. The product of Formula I is then isolated and purified by techniques well known in the art, such as extraction techniques. For example, the reaction mixture concentrated under vacuum and the residue dissolved in water or ethyl acetate and washed with methylene chloride. The aqueous is then acidified with a suitable acid, such as HCl and the product of Formula I is then extracted with suitable organic solvents, such as methylene chloride and diethyl ether. The organic extracts are then purified utilizing techniques known in the art, such as drying over anhydrous sodium or magnesium sulfate, followed by filtration and concentration under reduced pressuer to provide the compound of Formula I.

It will be recognized by one of skill in the art that the individual steps in the following examples may be varied to provide the compound of Formula I. The particular order of steps required to produce the compound of Formula I is dependent upon the particular intermediate being synthesized, the starting compound, and the relative lability of the substituted moieties. The reagents and starting materials are readily available to one of ordinary skill in the art. Nomenclature for examples set forth herein with AutoNom 2000 Add-in for MDL® ISIS/Desktop. As used herein, the terms listed in the following table have the corresponding meanings as indicated:

| TERM | MEANING |
| --- | --- |
| MS(ES) | Electron spray mass spectrometry |
| $^1$H NMR | Proton nuclear magnetic resonance spectrometry |
| TLC | thin layer chromatography |
| HPLC | high performance liquid chromatography |
| RT | room temperature |
| DMF | N,N-dimethylformamide |
| DMSO | dimethyl sulfoxide |
| EtOAc | ethyl acetate |
| DBU | 1,8-diazabicyclo[5.4.0]undec-7-ene |
| $Et_3N$ | triethylamine |
| $(Boc)_2O$ | di-tert-butyl dicarbonate |
| (dppf) | 1,1'-bis(diphenylphosphino)ferrocene |
| $Pd(PPh_3)_4$ | Tetrakis-(triphenylphosphan)-palladium |
| $Pd(PCy_3)_2Cl_2$ | dichlorobis(tricyclohexylphosphine) palladium (II) |

As shown in Step 1 of Scheme 1, Compound (c) is prepared by coupling a suitable aryl halide, such as compound (a) with a suitable aryl boronic ester (b), under Suzuki-Type or Stille-Type coupling reaction conditions well known to one of ordinary skill in the art. See Suzuki, A., *Journal of Organometallic Chemistry*, 576, 147-168 (1999), and Miyaura and Suzuki, *Chemical Reviews*, 95, 2457-2483 (1995) for examples of

Preparation 1

Propane-2-sulfonic acid{2-[4-(4,4,5,5-tetramethyl-[1,3,2,]dioxaborolan-2-yl)-phenyl]-thiophen-3-yl}-amide

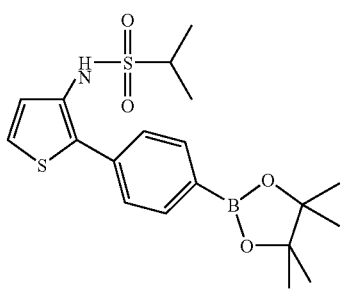

In a manner analogous to the method of Barker, J. M.; et al., *Synthetic Communications*, 25(23), 3729-3734 (1995), reflux (120° C.) methyl-3-aminothiophene-2-carboxylate (42.8 g, 0.27 mol) with 2M sodium hydroxide aqueous solution (270 mL) for 30 min. Cool the reaction mixture to 0° C. and acidify to pH 5.0 (Congo red) with concentrated hydrochloric acid. Filter the thick precipitate. Dry the solid and dissolve in acetone (300 mL) and dry the resulting solution (MgSO$_4$), filter, and evaporate at 20° C. Treat the resulting thick oil instantly with oxalic acid dihydrate (26.7 g) in 2-propanol (100 mL) at 38° C. for 45 min. Allow the mixture to reach room temperature and dilute with diethyl ether (40 mL). Filter the solid and wash with diethyl ether. The resulting white solid (33.1 g) becomes pale lilac on exposure to light and air. Dissolve the resulting salt (33.1 g) in water (400 mL) and basify with concentrated ammonium hydroxide. Extract the mixture with methylene chloride (3×200 mL) and combine the extract and dry (MgSO$_4$), filter, and evaporate to give a brown oil (15 g, 56%). Dissolve this material (15 g, 0.15 mol) in methylene chloride (300 mL) and add Et$_3$N (42.2 mL, 0.3 mol) at 0° C. Add a solution of (Boc)$_2$O (39.3 g, 0.18 mol) in methylene chloride (100 mL) dropwise at 0° C. and stir the mixture overnight at room temperature. Monitor TLC (Hexane/EtOAc 9:1) for complete disappearance of starting material. Quench the reaction by addition of water (200 mL). Extract the mixture with methylene chloride (2×200 mL) and combine the extracts, dry (MgSO$_4$), filter, and evaporate. Purify the crude by flash chromatography (Silica gel-Hexane/EtOAc 9:1) to obtain 20.1 g (67%) of (tert-butoxy)-N-(3-thiophenyl)carboxamide as a white solid.

In a manner analogous to Campaigne, E. and Monroe, P. A. *J.A.C.S.*, 76, 2447-2450 (1954), to a boiling solution of (tert-butoxy)-N-(3-thiophenyl)carboxamide (21.0 g, 0.1 mol) in methylene chloride (400 mL) add N-iodosuccinimide (23.7 g, 0.1 mol) in small portions. Set the heating bath to 65° C. for 20 min. Take the reaction to room temperature, evaporate the solvent and purify the crude by flash chromatography (Silica gel-Hexane/EtOAc 9:1) to obtain 30.0 g (88%) of (tert-Butoxy)-N-(2-iodo(3-thiophenyl))carboxamide as a white solid.

Heat (tert-Butoxy)-N-(2-iodo(3-thiophenyl))carboxamide (16.88 g, 0.52 mol), 4-bromophenylboronic acid (15.65 g, 0.78 mol), Na$_2$CO$_3$ (1.01 g, 1.04 mol) and Pd(PPh$_3$)$_4$ (5.79 g, 0.052 mol) in 375 ml of an anhydrous and deoxygenated 2:1 DME/EtOH mixture to 80° C. under nitrogen atmosphere for 24 h. Evaporate the organic solvents prior to the addition of water (200 mL). Extract the mixture with methylene chloride (3×150 mL) and combine the organic phases, dry (anh MgSO$_4$), filter, and concentrate to furnish a crude mixture as a yellowish solid. Purification by flash chromatography (Silica gel-Hexane/EtOAc 49:1) yields 10.8 g (60%) of (tert-butoxy)-N-[2-(4-bromophenyl)(3-thiophenyl)]carboxamide as a pale yellow solid.

Treat dropwise a solution of (tert-butoxy)-N-[2-(4-bromophenyl)(3-thiophenyl)]carboxamide (10.8 g, 0.3 mol) in EtOAc (75 mL) at 0° C. with 244 mL (8 mL/mmol) of freshly prepared 1N HCl in EtOAc and stir the mixture at room temperature overnight. Dissolve the white precipitate with H$_2$O (100 mL) and neutralize with a NaHCO$_3$ saturated solution. Extract the mixture with EtOAc (3×100 mL) and combine organic, dry and concentrate to give a slightly colored solid. Purification of the crude material by flash chromatography (Silica gel-Hexane/AcOEt 49:1 then 9:1) furnishes 5.7 g (74%) of 2-(4-bromo-phenyl)-thiophen-3-yl amine as a pale yellow solid.

Add slowly to a solution of 2-(4-bromo-phenyl)-thiophen-3-yl amine(0.6 g, 2.36 mmol) in dry dichloromethane (10 mL) at 0° C., DBU 1.41 mL (9.45 mmol) and isopropylsulfonyl chloride (0.53 mL, 4.72 mmol) (Temp. always <0° C.). Remove the ice bath and stir the mixture at RT overnight. Add satd. aq. NH$_4$Cl (10 mL) and extract the solution with EtOAc (2×10 mL). Dry the combined organic layers and concentrate under vacuum. Purify the crude residue by flash chromatography (Silica gel-Hexane/EtOAc 4:1) to give 0.8 g (94%) of propane-2-sulfonic acid [2-(4-bromo-phenyl)-thiophen-3-yl]-amide.

Deoxygenate by purging with nitrogen a mixture of propane-2-sulfonic acid [2-(4-bromo-phenyl)-thiophen-3-yl]-amide (1.34 g, 3.72 mmol), bis(pinacolato)diboron (1.04 g, 4.09 mmol), KOAc (1.21 g, 12.3 mmol) and Pd(dppf)Cl$_2$ (0.3 g, 0.37 mmol) in dry DMF (20 mL) and heat the mixture to 80° C. overnight. Add water (20 mL) and extract the reaction with diethyl ether (3×20 mL). Wash the combined organics with water and dry and concentrate to give a crude dark solid. Purification by flash chromatography (Silica gel-Hexane/AcOEt 7:1) gives 0.65 g (43%) of the title compound as a pale yellow solid.

Preparation 2

Propane-2-sulfonic acid {2-[4-(4,4,5,5-tetramethyl-[1,3,2]dioxaborolan-2-yl)-phenyl]-thiophen-3-yl}-amide Add bis(pinacolato)diboron (1.10 equiv; 215.2 moles), propane-2-sulfonic acid [2-(4-bromo-phenyl)-thiophen-3-yl]-amide (1.00 equiv, 191.52 moles), N,N-Dimethylformamide (325.2 L) and Potassium Acetate (570.89 moles; 3 equiv) to a nitrogen flushed reactor. Add Pd(dppf)Cl$_2$ (3.38 moles; 0.04% w/w, 2.76 kg) and heat the mixture to 75-90° C. for one hour. Maintain temperature at approximately 87° C. for ten hours. Cool to 30° C., then add ethyl acetate (619.8 kg) and water (1035 kg) and stir for 0.5 h. Allow mixture to stand for 1.5 h, then add NaCl to facilitate phase separation. Stir for 15 minutes then allow phases to separate. Separate layers, then treat organic layer with activated carbon and heptane. Heat mixture to 55-60° C. for 20 minutes, then filter over diatomaceous earth. Rinse with EtOAc/n-heptane. Concentrate filtrate under reduced pressure, add water, then concentrate under reduced pressure again. Add methanol, then filter to obtain the title compound. (86% yield).

Preparation 3

3-Ethoxy-4-iodo-benzoic acid ethyl ester

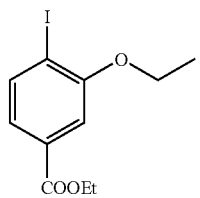

Dissolve 3-hydroxy-4-iodobenzoic acid (2.02 g, 7.65 mmol) in ethanol saturated with HCl gas (50 ml). Heat the solution under reflux overnight. Evaporate ethanol to yield 3-Hydroxy-4-iodo-benzoic acid ethyl ester compound (97% yield).

Reflux 3-hydroxy-4-iodo-benzoic acid (38 g, 144 mmol) and saturated solution of HCl in ethanol (600 mL) overnight. Evaporate the solvent yielding 42 g, 99% of 3-hydroxy-4-iodo-benzoic acid ethyl ester. $^1$H NMR (300 MHz, CDCl$_3$): δ 1.39 (t, J=7.1 Hz, 3H), 4.36 (q, J=7.1 Hz, 2H), 7.33 (dd, J=8.3 and 2.0 Hz, 1H), 7.64 (d, J=2.0 Hz, 1H), 7.75 (d, J=8.3 Hz, 1H). Add ethyl iodide (33.8 g, 216 mmol) to a solution of 3-hydroxy -4-iodo-benzoic acid ethyl ester (42 g, 144 mmol) and K$_2$CO$_3$ (39.9 g, 288 mmol) in acetonitrile (400 mL) under magnetic stirring. Heat the reaction mixture at 65° C. for 2 hours, allow the mixture to cool and maintain at RT overnight. Evaporate the solvent and add ethyl acetate to the crude. Filter the solid through Celite® and evaporate the solvent. Yield 42 g, 96%. $^1$H NMR (300 MHz, CDCl$_3$): δ 1.39 (t, J=7.1 Hz, 3H), 1.50 (t, J=7.0 Hz, 3H), 4.16 (q, J=7.0 Hz, 2H), 4.37 (q, J=7.1 Hz, 2H), 7.36 (dd, J=8.1 and 1.8 Hz, 1H), 7.42 (d, J=1.8 Hz, 1H), 7.84 (d, J=8.1 Hz, 1H).

EXAMPLE 1

2-Ethoxy-4'-[3-(propane-2-sulfonylamino)-thiophen-2-yl]-biphenyl-4-carboxylic acid

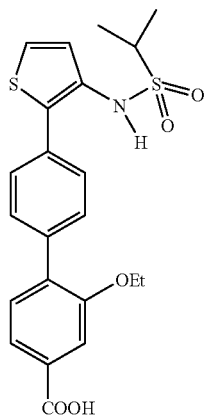

Mix propane-2-sulfonic acid {2-[4-(4,4,5,5-tetramethyl-[1,3,2]dioxaborolan-2-yl) -phenyl]-thiophen-3-yl}-amide, 3-ethoxy-4-iodo-benzoic acid ethyl ester (31.5 g, 98.3 mmol), PdCl$_2$(dppf) (4 g, 4.9 mmol), Na$_2$CO$_3$ 2M in water (98 mL), DME (550 mL), ethanol (180 mL) under a N$_2$ atmosphere and heat the reaction mixture at 60° C. overnight. Evaporate most of the solvent, and add to the crude CH$_2$Cl$_2$ (400 mL) and water (300 mL). Separate the organic layer, dry over magnesium sulphate and evaporate the solvent. Triturate the crude with hexane and filter the solid.

The resultant ester may be hydrolyzed in the following manner: Mix 2-ethoxy-4'-[3-(propane-2-sulfonylamino)-thiophen-2-yl]-biphenyl-4-carboxylic acid ethyl ester (38 g, 80 mmol), in ethanol (100 mL) and NaOH 2 M in water (400 mL) and stir the reaction mixture for one hour at RT. Evaporate the ethanol and wash the aqueous mixture with 200 mL of EtOAc. Acidify the aqueous mixture to pH 2 using HCl 1N. Extract the desired product with EtOAc. Dissolve the crude in warmed acetone (500 ml) and add water (600 ml), maintaining the temperature at 55° C. Stir the mixture at 60° C. for 1 hour and then to RT. overnight. Filtrate the precipitate and dry under vacuum at 45° C. overnight. Yield 28 g, 78%. $^1$H NMR (300 MHz, DMSO): δ 1.14 (d, J=7.0 Hz, 6H), 1.31 (t, J=7.0 Hz, 3H), 3.06 (sept, J=7.0 Hz, 1H), 4.13 (q, J=7.0 Hz, 2H), 7.10 (d, J=5.3 Hz, 1H), 7.48 (d, J=7.6 Hz, 1H), 7.54 (d, J=5.3 Hz, 1H), 7.58-7.68 (m,4H), 7.72 (d, J=8.4 Hz, 2H), 9.22 (bs, 1H), 13.04 (bs, 1H).

EXAMPLE 2

2-Ethoxy-4'-[3-(propane-2-sulfonylamino)-thiophen-2-yl]-biphenyl-4-carboxylic acid Mix propane-2-sulfonic acid {2-[4-(4,4,5,5-tetramethyl-[1,3,2]dioxaborolan-2-yl) -phenyl]-thiophen-3-yl}-amide (1.00 equiv; 441.02 mmoles; 196.60 g), 3-ethoxy-4-iodo -benzoic acid ethyl ester (1.00 equiv; 441.47 mmoles; 141.27 g), DME (15.15 moles; 1.57 L; 1.37 kg), PdCl$_2$(dppf) (2.42 mmoles; 1.97 g), and ethanol (13.57 moles; 790.00 mL; 625.13 g) under a N$_2$ atmosphere. Then add Na$_2$CO$_3$ 2M in water (1.89 equiv; 833.06 mmoles; 416.53 mL; 504.00 g) and heat the reaction mixture to reflux until HPLC monitoring indicates reaction completion. Cool reaction mixture to RT then add water (109.13 moles; 1.97 L). Separate the organic layer, filter through diatomaceous earth, then concentrate organic layer under reduced pressure. Add ethanol (2.36 L), and remove solvent under reduced pressure. Add 3-Mercaptopropyl-functionalized Silica Gel (50.00 g), and heat to 60° C. for 30 minutes. Cool to RT then filter over diatomaceous earth. Rinse cake with ethanol, then combine ethanol washes and filtrate. Add 14% Sodium Hydroxide (4.89 moles; 1.27 L; 1.43 kg) and heat the reaction mixture at 55° C. until monitoring by HPLC indicates the end of the reaction. Cool to RT then add 7N HCl to the reaction mixture. Stir the resulting precipitate overnight. Filter the reaction mixture and wash cake with EtOH/Water (40/60-v/v) (180.78 g), EtOH (155.49 g), and n-heptane (262 g). Redissolve cake in acetone (2.18 kg) and add activated charcoal (46 g). Heat the reaction mixture at 50° C. for 30 minutes. Cool to RT, filter over diatomaceous earth (765.59 mmoles; 200.00 g), and concentrate under reduced pressure. Cool to RT, then add n-Heptane (7.73 moles; 1.13 L; 775. 00 g) and stir for 1 h. Fltere and wash cake with n-heptane/acetone 60/40 (2.58 moles; 354.79 mL) and dry under reduced pressure to yield 124 g of the title compound.

General Procedure for the Preparation of Salts and Crystals

A master plate is prepared with 250 μL of the free acid of the subject compound in methanol (0.1 M) added to all wells set in a 96 well format. An array of bases is dispensed to each well in one and two molar equivalents. The solvents are evaporated from all 96 wells using a Genevac Series II evaporator leaving solid residue in the master plate. An array of solvents is dispensed to each one of these wells through a cap mat and then heated to 55° C. with stirring and allowed to equilibrate for 60-90 minutes at about 55° C. Each sample is then filtered hot and transferred to corresponding wells in an evaporation plate, a precipitation plate, and a cooling plate. The evaporation plate is prepared by transferring 200 μL of the filtrate from the master plate using 55° C. heated syringes to the open well titer plate and is then allowed to evaporate to dryness over night at room temperature and ambient humidity. The precipitation plate is prepared by adding 100 μL of the filtrate from the master plate using 55° C. heated syringes to capped 96 well titer plate where each well contains an antisolvent of 200 μL of heptane or 2-propanol. After equilibrating for a period of nine hours at room temperature, the excess solution is wicked away using pre-cut Whatman filter paper. The cooling plate is prepared by transferring 200 μL of the filtrate from the master plate to individual wells using 55° C. heated syringes in a capped titer plate, and cooling exponentially from 55 to 10° C. over a period of 8 hours. Photomicrographs are collected on the material at the bottom of each well in the 96 well plates using a Zeiss Axiovert 200M inverted incident-light microscope with a 2.5× objective. If the material is crystalline, it exhibits birefringence that is displayed as white against a dark background. Amorphous solids appear dark or as opaque droplets or rings.

The ability of compounds of Formula I to potentiate glutamate receptor-mediated response can be determined by one of ordinary skill in the art. For example, see U.S. Pat. No. 6,303,816. In particular, the following test may be utilized:

HEK293 cells stably expressing human iGluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 MgCl2, 10 HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg-1. With these solutions, recording pipettes have a resistance of 2-3 MΩ. Using the whole-cell voltage clamp technique (Hamill et al. (1981) Pflügers Arch., 391: 85-100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined. The compound prepared in Example 1 was tested and found to have an activity of 0.145 μM.

In addition, certain behavioral despair animal models, which can be practiced by one of ordinary skill in the art to evaluate compounds of the present invention, are predictive of antidepressant activity in man, such as the Forced Swim Test and the Tail Suspension Test. For example, see "*Experimental Approaches to Anxiety and Depression*", Edited by J. M. Elliott, et al., (1992), John Wiley & Sons Ltd., Chapter 5, *Behavioural Models of Depression*, Porsolt and Lenegre, pages 73-85.

The pharmaceutical compositions of the present invention are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 0.1 mg to about 300 mg, preferably about 0.1 mg to about 100 mg, and most preferably about 1.0 to about 100 mg of compound of Formula I. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

As used herein the term "patient" refers to a mammal, such as a mouse, guinea pig, rat, dog or human. It is understood that the preferred patient is a human.

As used herein, the terms "treating" or "to treat" or "treatment" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of Formula I which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I can be administered by a variety of routes including oral, rectal, transdermal, subcutaneous, intravenous, intramuscular, bucal or intranasal routes. Alternatively, the compound of Formula I may be administered by continuous infusion. A typical daily dose will contain from about 0.005 mg/kg to about 10 mg/kg of the compound of Formula I. Preferably, daily doses will be about 0.005 mg/kg to about 5 mg/kg, more preferably from about 0.005 mg/kg to about 2 mg/kg.

The dosages of the drugs used in the combinations set forth herein, must also, in the final analysis, be set by the physician in charge of the case, using knowledge of the drugs, the properties of the drugs in combination as determined in clinical trials, and the characteristics of the patient, including diseases other than that for which the physician is treating the patient.

The inert ingredients and manner of formulation of the adjunctive pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment.

For example, a formulation may include 1% carboxymethylcellulose sodium, 0.25% polysorbate 80 and 0.05% Dow Corning Antifoam 1510-US in purified water) through the oral route. For the IV administration, a composition of 5% pharmasolve, 0.4% 1N NaOH, 94.6% Dextrose 5% in water may be used.

I claim:

1. A compound of Formula I:

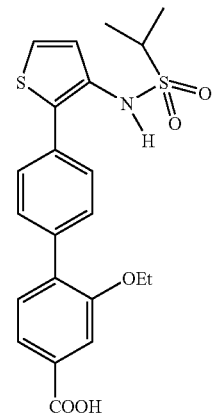

2-Ethoxy-4'-[3-(propane-2-sulfonylamino)-thiophen-2-yl]-biphenyl-4-carboxylic acid or a pharmaceutically acceptable salt thereof.

2. A pharmaceutical formulation comprising a compound of Formula 1:

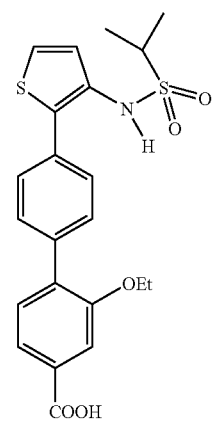

or a pharmaceutically acceptable salt thereof in combination with a pharmaceutically acceptable carrier, diluent or excipient.

* * * * *